US00PP19780P2

(12) United States Plant Patent
Danziger

(10) Patent No.: US PP19,780 P2
(45) Date of Patent: Mar. 3, 2009

(54) ***LOBELIA* PLANT NAMES 'DANANB3'**

(50) Latin Name: *Lobelia erinus*
Varietal Denomination: DANANB3

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,644

(22) Filed: Jan. 11, 2008

(51) Int. Cl.
*A01H 5/00* (2006.01)

(52) U.S. Cl. ..... Plt./451

(58) Field of Classification Search ..... Plt./451, Plt./263

See application file for complete search history.

*Primary Examiner*—Annette H Para
*Assistant Examiner*—S. B. McCormick-Ewoldt

(57) ABSTRACT

A new and distinct *Lobelia* cultivar named 'DANANB3' is disclosed, characterized by having lilac flowers flowers, trailing plant habit, highly floriferous flowering and a day-neutral flowering habit. The new variety is a *Lobelia*, normally produced as an outdoor garden or container plant.

2 Drawing Sheets

Figure 1:
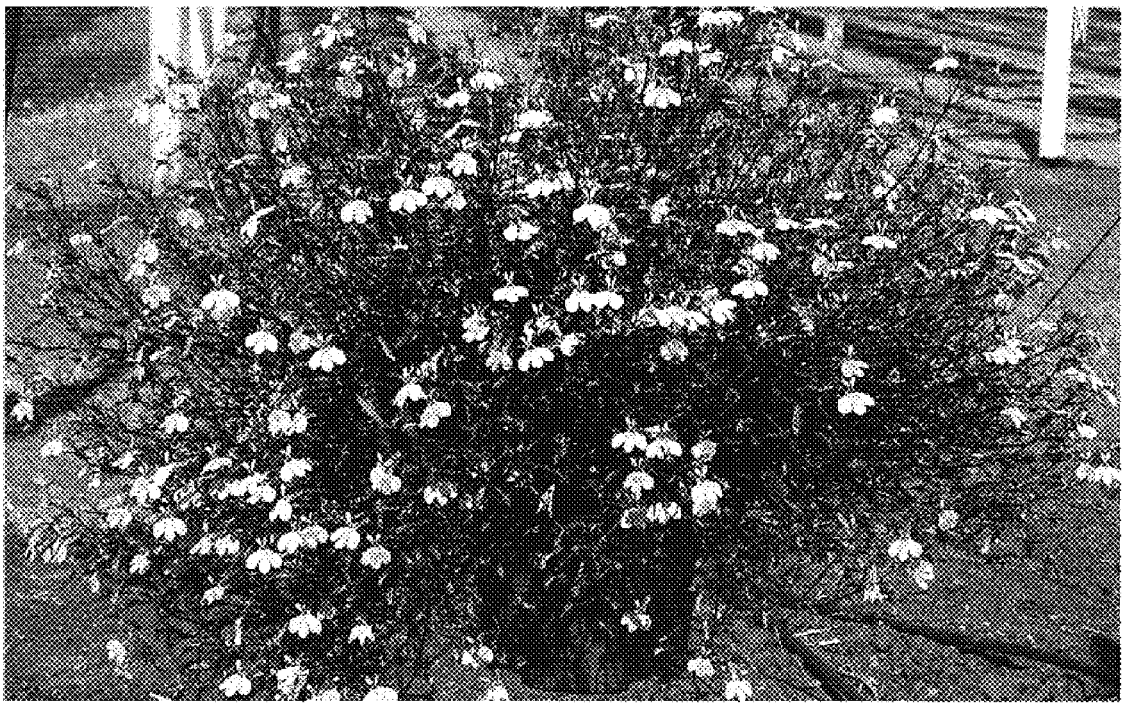

Latin name of the genus and species: *Lobelia erinus*.
Variety denomination: 'DANANB3'.

BACKGROUND OF THE INVENTION

The new *Lobelia* cultivar is a product of a planned breeding program conducted by the inventor, Gabriel Danziger, in Moshav Mishmar Hashiva, Israel. The objective of the breeding program was to produce new trailing perennial *Lobelia* varieties. The seed parent is the unpatented, proprietary seedling variety referred to as *Lobelia erinus* 'LOB-6-369.' The pollen parent is the unpatented, proprietary seedling variety referred to as *Lobelia erinus* 'LOB-6-401.' The new variety was discovered in April 2005 by the inventor in a group of seedlings resulting from that crossing, in a commercial greenhouse in Moshav Mishmar Hashiva, Israel.

Asexual reproduction of the new cultivar 'DANANB3' by vegetative cuttings was first performed at a commercial greenhouse in Moshav Mishmar Hashiva, Israel in April 2005. Subsequent propagation has shown that the unique features of this cultivar are stable and reproduced true to type on successive generations.

SUMMARY OF THE INVENTION

The cultivar 'DANANB3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANANB3' These characteristics in combination distinguish 'DANANB3' as a new and distinct *Lobelia* cultivar:

1. Trailing plant habit
2. Highly floriferous.
3. Day-neutral flowering.

Plants of the new cultivar 'DANANB3 ' are similar to plants of the parent, *Lobelia erinus* 'LOB-6-369' in most horticultural characteristics, however, plants of the new cultivar 'DANANB3' are trailing, compared to an erect habit of the female parent. Additonally, plants flowers of the new variety have a lighter, lilac/pink colored flower, compared to the purple flower color of the female parent.

Plants of the new cultivar 'DANANB3' are similar to plants of the parent, *Lobelia erinus* 'LOB-6-401' in most horticultural characteristics, however, plants of the new cultivar 'DANANB3' have a mounding habit, compared to the trailing habit of the pollen parent. Additionally, plants of the new variety have matte textured foliage, while the pollen parent has shiny leaves. The new variety has a lilac/pink colored flower, compared to the white flower of the male parent.

COMMERCIAL COMPARISON

Plant of the new cultivar 'DANANB3' are best compared to the commercial variety 'WESLOSPOT,' U.S. Plant Pat. No. 15,835. 'DANANB3' are similar to 'WESLOSPOT' in most horticultural characteristics, however, 'DANANB3' plants have a trailing habit compared to the erect habit of 'WESLOSPOT.' Additionally, plants of 'DANANB3' have thinner, more flexible branches, than plants of 'WESLOSPOT.' Also, flowers of 'DANANB3' are lilac, compared to blue and white bi-color of 'WESLOSPOT.'

BRIEF DESCRIPTION OF THE PHOTOGRAPH

The accompanying photograph in FIG. 1 illustrates in full color a typical plant of 'DANANB3' grown in a greenhouse, in a 12 cm pot. Age of the plant photographed is approximately 90 days from a rooted cutting.

Figure 2:
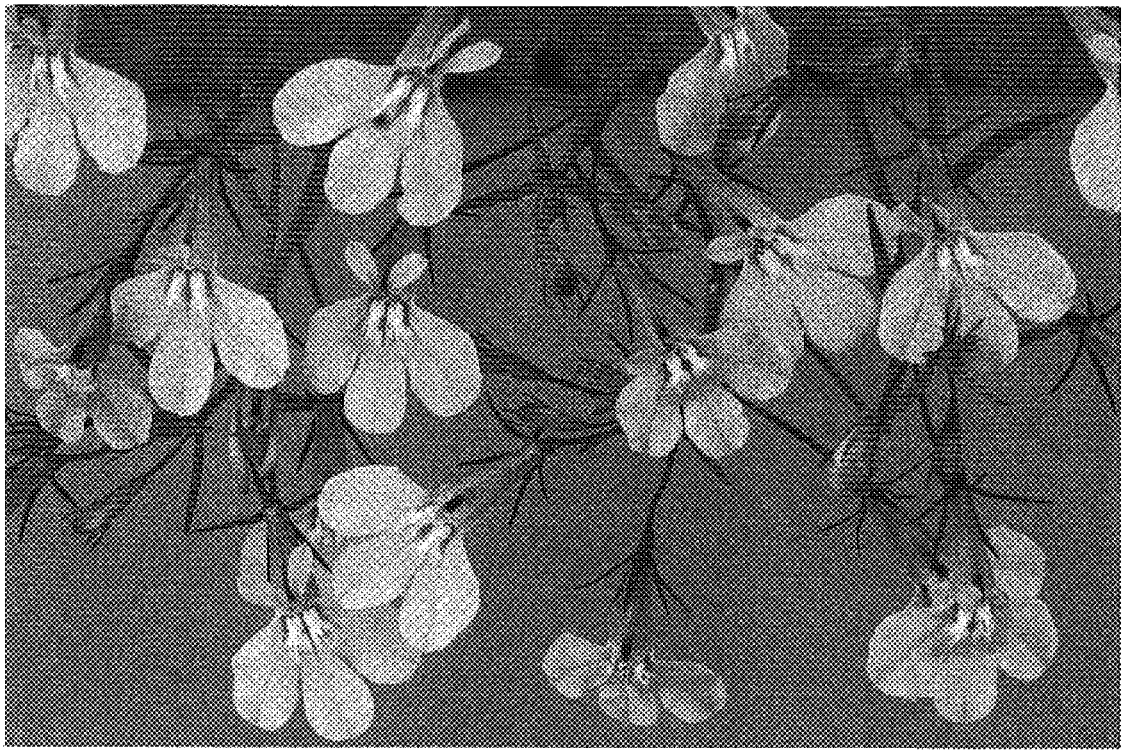

FIG. 2 illustrates in full color a close up of a typical bloom of 'DANANB3.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANANB3' plants grown in a greenhouse in Moshav Mishmar Hashiva, Israel. The growing temperatures ranged from 20° C. to 28° C. The greenhouse is un-shaded, giving bright, normal sunlight conditions. Measurements and numerical values represent averages of typical plant types.

Botanical classification: *Lobelia erinus* cultivar 'DANANB3.'

PROPAGATION

Time to initiate roots: About 5 days at approximately 15–30° C.
Root description: Fine, densely fibrous.
Time to produce a rooted cutting: About 15 days at 15–30° C.

PLANT

Growth habit: Trailing.
Pot size of plant described: 10 cm.
Height:
*To top of flowers.*—Approximately 10–14 cm.
Plant spread: Approximately 20 cm.
Growth rate: Rapid.
Branching characteristics: Free-branching.
Length of primary branches: Approximately 30 cm.
Length of secondary branches: Approximately 13 cm.
Diameter of primary branches: Approximately 0.4 cm.
Quantity of primary and secondary branches: About 50.
Color of primary branches: Near RHS Green 1379a.
Texture: Glabrous.
Internode length: Approximately 3 cm.
Age of plant described: Approximately 60 days from a rooted cutting.

FOLIAGE

Arrangement: Alternate.
Basal leaves:
*Size.*—Length: About 5 cm. Width: About 2 cm. Shape of leaf: Obovate. Shape of apex: Obtuse. Shape of base: Cuneate. Texture: Glabrous. Aspect: 90 degrees. Margin type: Serrate.
Midplant leaves:
*Size.*—Length: About 4.5 cm. Width: About 0.8 cm. Shape of leaf: Ligulate. Shape of apex: Abruptly acute. Shape of base: Acuminate. Texture: Glabrous. Aspect: 45 to 90 degrees. Margin type: Serrate.
Apical leaves:
*Size.*—Length: about 2.5 cm. Width: about 0.3 cm.
*Shape of leaf.*—Ligulate.
*Shape of apex.*—Acute.
*Shape of base.*—Cuneate.
*Texture.*—Glabrous.
*Aspect.*—90 degrees.
*Margin type.*—Entire.
*Color.*—Young leaves: Upper surface: RHS Green 137C. Lower surface: RHS Green 137D. Mature leaves: Upper surface: RHS Green 137C. Lower surface: RHS Green 137D.
*Petiole.*—None.
*Veins.*—Venation pattern: Palmate. Color: Upper surface: RHS Green 137A. Lower surface: RHS Green 137B.

FLOWER

Natural flowering season: Flowering occurs continuously during growing season from spring until fall under Israeli climatic conditions. Flowering begins approximately 3 weeks after planting a rooted cutting.
Flower type and habit: Flowers arranged singly at lateral apices.
Number of flowers per plant: Approximately 50.
Fragrance: None.
Longevity: Depending on weather conditions, 7–14 days for single flower. Flowering season for the entire plant lasts approximately 250 days.
Flower size:
*Tube length.*—1 cm.
*Diameter.*—Distal end: 0.6 cm. Proximal end: 0.4 cm.
Flower shape and petal arrangement: Tubular with three larger lower petals and two upright petals.
*Bud.*—Stage of development when described: (about 4 days prior to opening): Shape: Spatulate. Diameter: About 0.2 cm. Length: About 1.2 cm. Color: Near RHS Yellow-Green 149B.
Petals:
*Arrangement.*—Single whorl of five petals, not fused; three larger lower petals, two smaller upper petals.
*Quantity.*—3 larger lower petals and 2 smaller upper petals.
*Length.*—Lower petals: About 1.2 cm. Upper petals: About 0.6 cm.
*Width.*—Lower petals: 0.7 cm. Upper petals: 0.2 cm.
*Shape.*—Lower petals: Broadly oblong. Upper petals: Oblanceolate.
*Apex.*—Cuspidate.
*Base.*—Cuneate.
*Margin.*—Entire.
*Texture.*—Smooth.
*Color.*—When opening: RHS Violet 84D. Fully opened: RHS Violet 84D.
*Throat.*—Veination: RHS Violet 84A.
*Tube.*—Veination: RHS Yellow-Green 144C.
Sepals:
*Arrangement.*—Single whorl of five sepals, star-shaped calyx.
*Length.*—About 0.65 cm.
*Shape.*—Apiculate.
*Apex.*—Acute.
*Margin.*—Entire.
*Texture.*—Upper and lower surfaces: Pubescent.
*Color.*—Upper surface: 147A Lower surface: Yellow-Green 147A.
Peduncles:
*Length.*—About 3.5 cm.
*Diameter.*—About 0.7 mm.
*Color.*—147A.
*Texture.*—Sparsely pubescent to glabrous.
*Orientation.*—Angled.
*Strength.*—Wiry, flexible.

REPRODUCTIVE ORGANS

Stamens:
*Number (per flower).*—5 fused.
*Filament length.*—About 0.8 cm.
*Anthers.*—Shape: Ellipsoid. Length: About 0.4 cm. Diameter: About 0.2 cm. Color: RHS Violet-Blue 95B.

Pollen:

*Color*.—RHS Greyed-Yellow 160A.

*Amount*.—Moderate.

Pistils:

*Quantity per flower*.—1.

*Length*.—About 0.8 cm.

*Styles*.—Length: About 0.5 cm. Color: Yellow-Green 146D.

*Stigma*.—Shape: Obovate. Color: Purple N79A. Ovary color: Yellow-Green 147B. Texture: Pubescent.

OTHER CHARACTERISTICS

Disease resistance: Neither resistance nor susceptibility observed.

Temperature tolerance: Tolerant to low temperature of about 2° C.

Seed and fruit production: Not observed and not commercially important.

What is claimed is:

1. A new and distinct cultivar of *Lobelia* plant named 'DANANB3' as herein illustrated and described.

* * * * *

UNITED STATES PATENT AND TRADEMARK OFFICE

CERTIFICATE OF CORRECTION

PATENT NO. : PP 19,780 P2
APPLICATION NO. : 12/008644
DATED : March 3, 2009
INVENTOR(S) : Gabriel Danziger It is certified that error appears in the above-identified patent and that said Letters Patent is hereby corrected as shown below:

Plant Name is misspelled. The Plant Name in the patent is 'Dananb3.'

The correct Plant Name is: 'Dananab3'

On the first page, under item 54, please replace 'Dananb3' with 'Dananab3'
On the first page, under item 50 Variety Denomination, please replace 'Dananb3' with "Dananab3'
On the first page, under item 57 ABSTRACT, please replace 'Dananb3' with 'Dananab3'

On the first page, on Column 1, line 16, please replace 'Dananb3' with 'Dananab3'
On the first page, on Column 1, line 25, please replace 'Dananb3' with 'Dananab3'
On the first page, on Column 1, line 32, please replace 'Dananb3' with 'Dananab3'
On the first page, on Column 1, line 33, please replace 'Dananb3' with 'Dananab3'
On the first page, on Column 1, line 38, please replace 'Dananb3' with 'Dananab3'
On the first page, on Column 1, line 41, please replace 'Dananb3' with 'Dananab3'

On the first page, on Column 2, line 3, please replace 'Dananb3' with 'Dananab3'
On the first page, on Column 2, line 6, please replace 'Dananb3' with 'Dananab3'
On the first page, on Column 2, line 14, please replace 'Dananb3' with 'Dananab3'
On the first page, on Column 2, line 16, please replace 'Dananb3' with 'Dananab3'
On the first page, on Column 2, line 19, please replace 'Dananb3' with 'Dananab3'

UNITED STATES PATENT AND TRADEMARK OFFICE

CERTIFICATE OF CORRECTION

PATENT NO. : PP 19,780 P2
APPLICATION NO. : 12/008644
DATED : March 3, 2009
INVENTOR(S) : Gabriel Danziger It is certified that error appears in the above-identified patent and that said Letters Patent is hereby corrected as shown below:

On the first page, on Column 2, line 21, please replace 'Dananb3' with 'Dananab3'
On the first page, on Column 2, line 27, please replace 'Dananb3' with 'Dananab3'
On the first page, on Column 2, line 31, please replace 'Dananb3' with 'Dananab3'

On the second page, on Column 3, line 1, please replace 'Dananb3' with 'Dananab3'

On the second page, on Column 6, line 11, please replace 'Dananb3' with 'Dananab3'

Signed and Sealed this

Twenty-fifth Day of August, 2009

David J. Kappos

David J. Kappos
*Director of the United States Patent and Trademark Office*